United States Patent
Hass

(10) Patent No.: US 10,952,636 B2
(45) Date of Patent: Mar. 23, 2021

(54) PLANAR POWER TRANSMITTER COIL WITH RUNGS

(71) Applicant: Sigwa Company, LLC, Acton, MA (US)

(72) Inventor: Kevin James Hass, Acton, MA (US)

(73) Assignee: Sigwa Company LLC, Acton, NJ (US)

( * ) Notice: Subject to any disclaimer, the term of this patent is extended or adjusted under 35 U.S.C. 154(b) by 0 days.

(21) Appl. No.: 16/542,708

(22) Filed: Aug. 16, 2019

(65) Prior Publication Data

US 2021/0045650 A1    Feb. 18, 2021

(51) Int. Cl.
| | |
|---|---|
| *A61B 5/055* | (2006.01) |
| *G01R 33/36* | (2006.01) |
| *G01R 33/38* | (2006.01) |
| *G01R 33/48* | (2006.01) |

(52) U.S. Cl.
CPC .......... *A61B 5/055* (2013.01); *G01R 33/3628* (2013.01); *G01R 33/3808* (2013.01); *G01R 33/4828* (2013.01)

(58) Field of Classification Search
CPC ................ A61B 5/055; G01R 33/4828; G01R 33/3628; G01R 33/3808
See application file for complete search history.

(56) References Cited

U.S. PATENT DOCUMENTS 4,714,886 A * 12/1987 Halpern ............... G01R 33/345
324/316

* cited by examiner

*Primary Examiner* — Susan S Lee
(74) *Attorney, Agent, or Firm* — Kanika Radhakrishnan; Evergreen Valley Law Group

(57) ABSTRACT

Disclosed herein are embodiments for a standing equine magnetic resonance imaging device. The device includes two opposing planar power transmit coils facing each other. Each of the planar power transmit coils includes a plurality of radio frequency conducting planar rungs arranged to form concentric circles and a plurality of radio frequency conducting planar spokes extending from an outermost rung and connecting to each of the rung circles. At least one pin diode is positioned across the outermost rung circle. A plurality of tuning capacitors are positioned across the spokes.

13 Claims, 6 Drawing Sheets

PLANAR POWER TRANSMITTER COIL WITH RUNGS

BACKGROUND

Technical Field

Embodiments generally relate to transmit coils for open magnetic resonance imaging, and in particular, to a planar transmit coil for an open MRI system.

Background

Magnetic Resonance Imaging (MRI) uses magnetic field and radio waves to produce detailed visual representations of the anatomy of a body, visualizing metabolic functions, and etc. for clinical diagnosis and medical intervention. The most important component of an MRI system is the magnet. Most commonly used magnets for MRI systems are superconducting magnets with horizontal tube internal bore for patients to lie inside during imaging. This type of magnet is also called a closed bore magnet. Some patients may get claustrophobia being moved inside the magnet tube. The tube magnet bore also present challenges for large imaging subjects to fit in. MRI imaging also requires cooperation of the image subjects to lie still, which is not possible for animals to lie inside and remain still in the tube without putting animals under general anesthesia that carry significant risk to the health of the animals. The magnet tube also presents difficulty for some applications, for example, imaging horse limbs. Another type of MRI system, an open MRI system, consists of an open bore magnet using permanent magnets in a C-shape or U-shape configuration. The open bore magnets have lower magnet field strength and image quality compared with the closed bore magnets but have the advantage of open bore for patient access and require no power consumption to be up at field. As an example, the U-shape permanent magnets can have the two flat magnetic plate sides, known as magnet poles, spaced apart by a predetermined distance to allow one horse lower limbs of a standing horse to be positioned therebetween for a standing equine MRI to evaluate health or any injuries, provided the magnet pole thickness is not too large to fit between the limbs of a horse. Typically, standing equine MRI images are taken of the horse's hooves. Standing equine MRI is performed on sedated horses, as the horses will move if it is startled or if the animal is standing in an uncomfortable position. During the MRI imaging the horse needs to stand still. Individual MRI sequences may take about 2 to 5 minutes, and the entire imaging session can take about one hour. During this time, if the animal is comfortable and sedated properly, it will stand still enough for the MRI imaging.

Radio wave frequency transmitter coils and receiving coils are essential MRI hardware components as they are responsible for the excitation and the reception of the MR signal. They directly impact the imaging spatial and temporal resolution, sensitivity, and uniformity in MRI. A radio frequency (RF) transmit coil generates an RF pulse that produces a small magnetic field perpendicular to the main magnetic field, which rotates net magnetization away from its alignment with the main magnetic field. Transmitter coils are resonant circuits that consists of electrical components that store electric (Capacitor) and magnetic energy (Inductor) to obtain an electromagnetic field when electric current flows.

BRIEF DESCRIPTION OF THE DRAWINGS

The accompanying drawings are incorporated herein and form a part of the specification.

DETAILED DESCRIPTION

Figure 1:
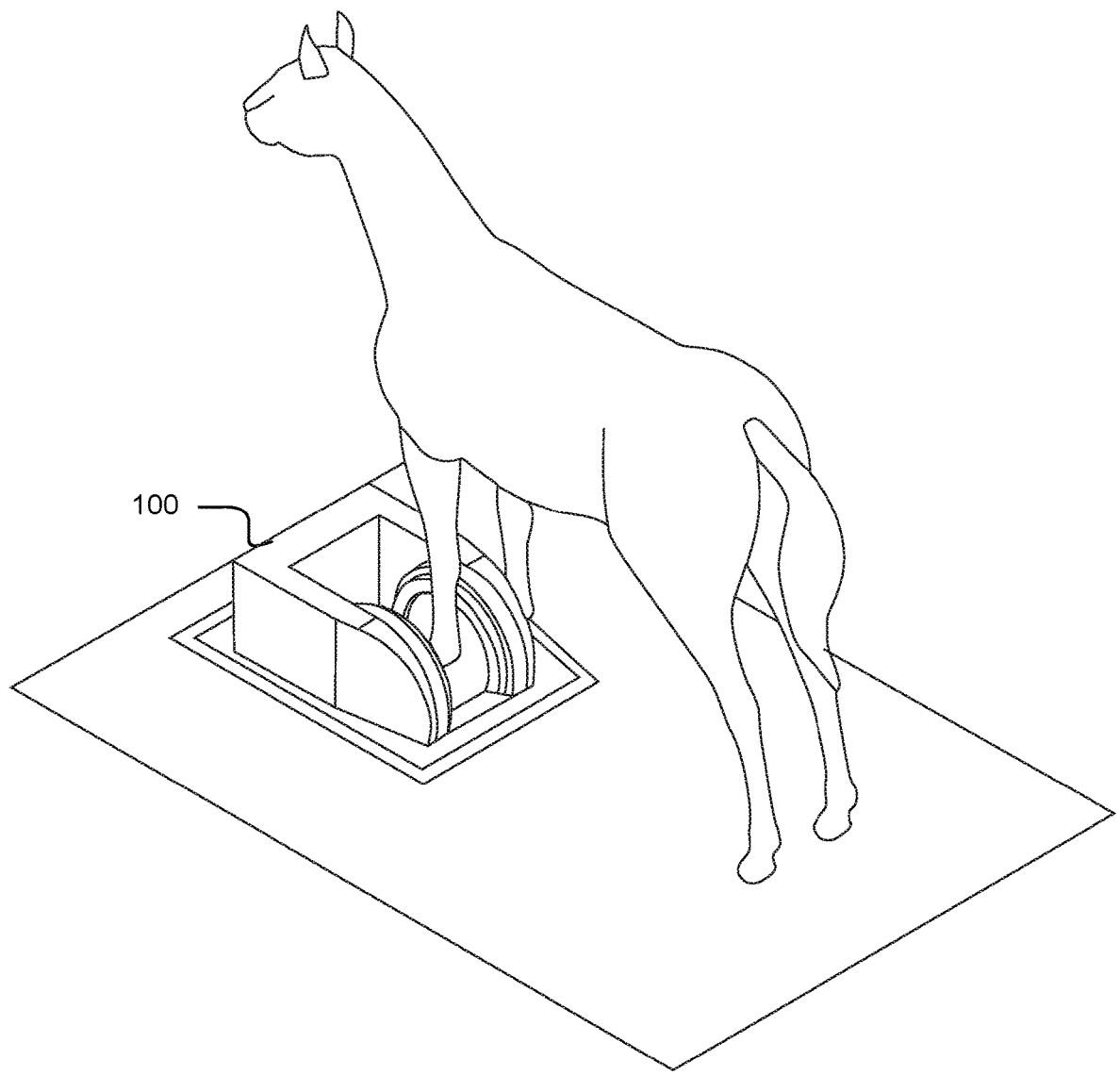
FIG. 1 illustrates a setup for the use of a standing equine MRI machine.
Figure 2:
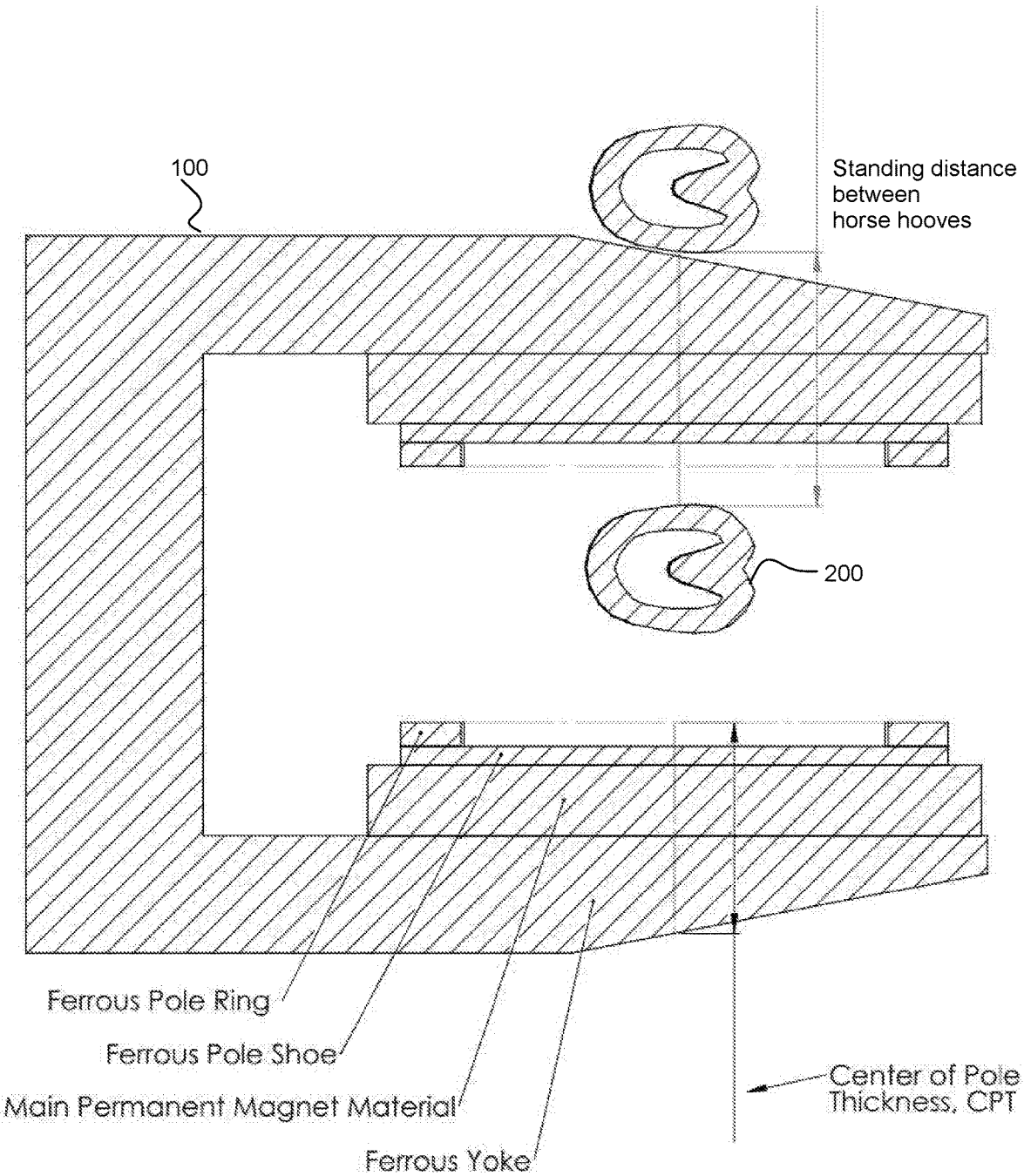
FIG. 2 shows a section view of an MRI magnet at the horse's hooves.

FIG. 1 shows a horse in position to be imaged in an MRI magnet 100. The magnet is lowered into a pit in the floor to allow the imaging at floor level. FIG. 2 shows a section view of the magnet at a horse's hoof 200. Magnet field strength is an important criterion for an MRI magnet. MRI imaging performance or signal to noise is directly proportional to magnet field strength. Higher field strength gives permanent magnets better imaging performance, but it requires more magnetic materials added on the two poles. As more magnetic materials are added to the poles, the poles get thicker, increasing the pole thickness. Standing equine MRI can use a permanent magnet to image one horse leg/hoof at a time, with one horse leg/hoof fit in the gap of a permanent magnet while the other leg/hoof comfortably standing outside the magnet on the side. Issues with standing equine MRI stem from horse anatomy, namely, that horses will stand comfortably when their legs are positioned about 7 inches (177.8 mm) apart. A horse will generally not stand comfortably if the legs are much further apart than 7 inches. Because the horse is imaged standing, this restricts the Center of the Pole Thickness (CPT) of a standing equine MRI magnet to a thickness smaller than this number. As such, the CPT is a critical design parameter for a standing equine MRI magnet because a horse needs to stand with this section of the MRI magnet between its legs during imaging. The CPT affects how far apart the horse's legs are during imaging. If the magnet CPT gets much larger, the magnet will not fit between the standing horse legs. If the CPT gets much smaller, it will have magnetic saturation causing magnetic field strength lower, resulting in reduced imaging performance. As such, the challenge in standing equine MRI design is to be able to have thin enough magnet CPT to fit between standing horse legs and still be able to have the pole thickness space for adding as much magnetic materials as possible to push the field strength as high as possible to give higher imaging performance.

Figure 3:
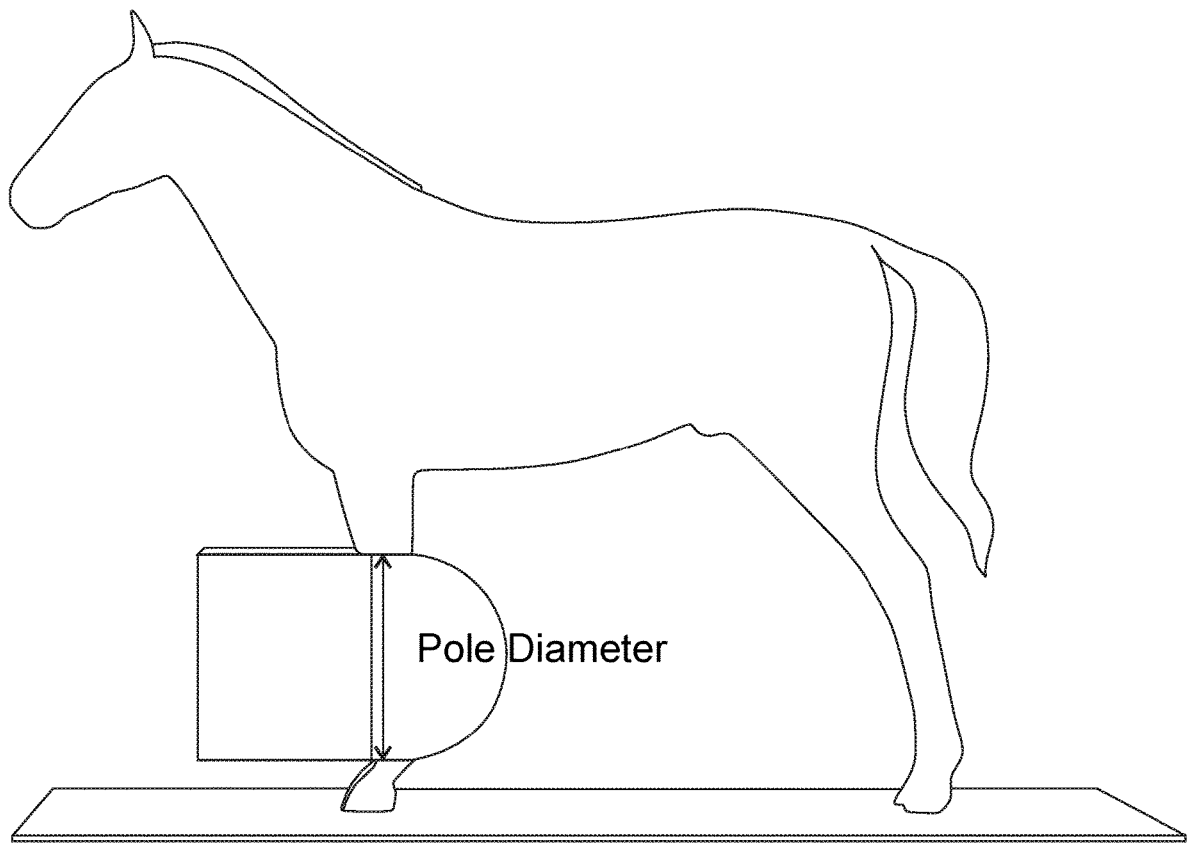
FIG. 3 shows a horse in a raised magnet.

Another way to add more magnetic materials therefore increasing field strength is to have larger pole diameter for more space to fit magnetic materials. However, having larger pole diameter is not desirable for standing equine MRI beyond added material cost. FIG. 3 shows the horse in a raised magnet. This allows imaging further up the horse's leg. The magnet height off the floor is limited by the pole diameter. The magnet can only be raised till it starts to touch the horse torso, so keeping the pole diameter smaller will allow the magnet to be raised higher. Thus, a compact MRI magnet may allow the horse to stand comfortably and permit imaging further up the horse's leg. The open MRI magnet's CPT includes the thickness of a ferrous yoke, a main permanent magnet material, a ferrous pole shoe, and a ferrous pole ring. This CPT is illustrated in FIG. 2. The ferrous pole shoe, ferrous pole ring, and ferrous yoke are typically made from steel, which saturates at a magnetic flux level of about 2 Tesla. As such, making the CPT thinner requires making these items thinner. The ferrous items can only be made thinner until they saturate with flux. Gradient coils, eddy current control plates, magnet passive shimming plates, any second-order shim coils, bore shields, and transmit coils are generally mounted on the pole shoes of open MRI systems. These components need to be kept as thin as possible to avoid increasing the CPT and decreasing the patient gap of open MRI systems.

Most commonly used transmit coils for open MRI systems are quadrature transmit coils. Quadrature transmit coils have two modes that are typically designed using two coils on each pole requiring two layers on each pole, increasing the thickness and complexity of the transmit coil, and resulting in decreasing the patient gap and increasing the CPT. While it may be possible to make the transmit coil as a large planar conducting surface, this large copper surface would introduce eddy currents into the gradient pulses creating imaging artifacts. Coils with a large planar conducting surface only have one current distribution that cannot be tailored to optimize the spatial RF field distribution and performance characteristics. The disclosed device advantageously fills these needs and addresses the aforementioned deficiencies by providing a thin single layer planar transmit coil on each pole that uses primarily circularly symmetric rungs, has more than one current distribution with tailored impedances and locations to control current flow and to provide a desired RF field spatial distribution and performance characteristics.

Figure 4:
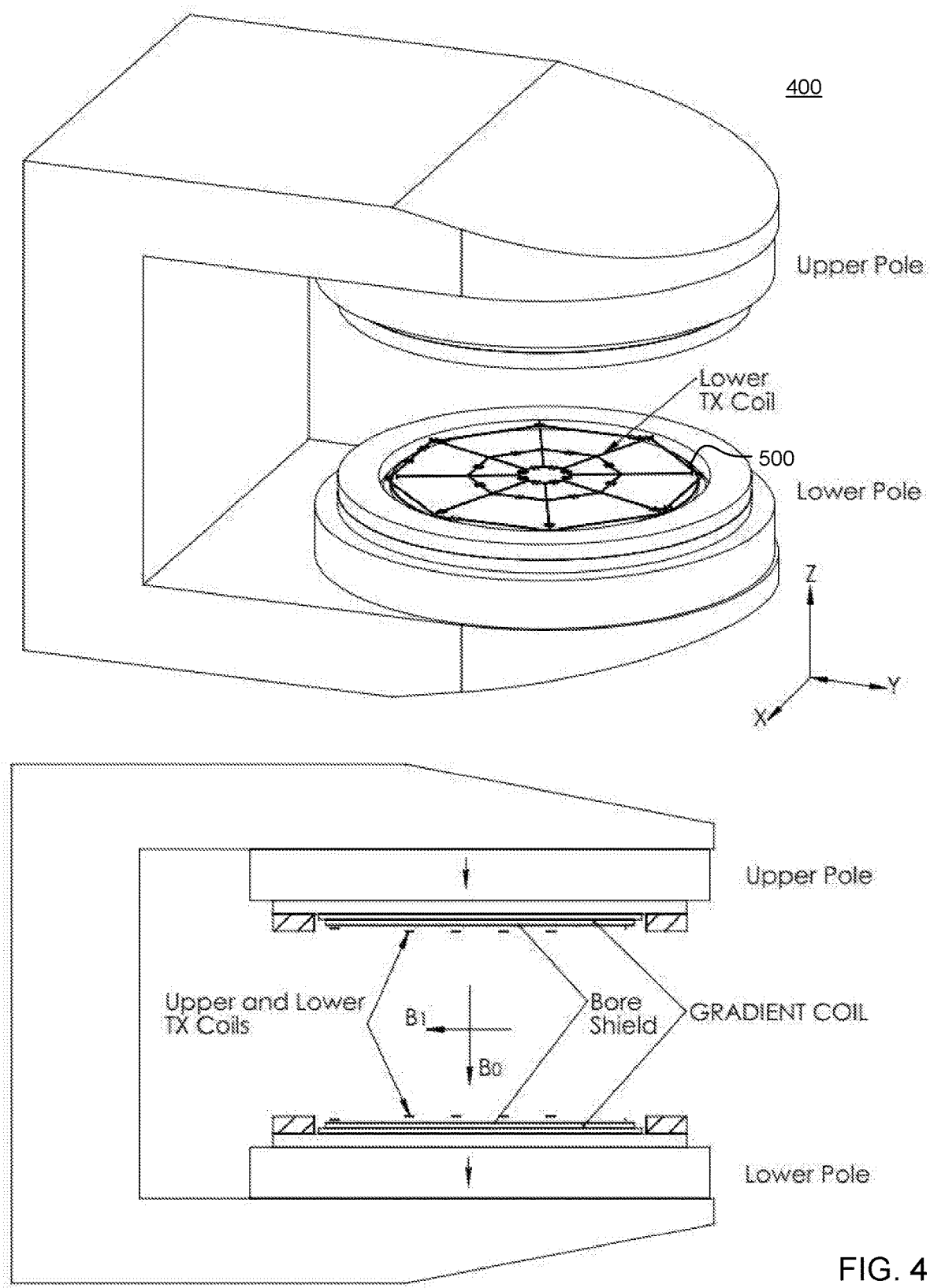
FIG. 4 shows an equine MRI device, according to an example embodiment.

FIG. 4 shows an equine MRI device 400, according to an example embodiment. MRI device 400 includes one opposing planar power transmit (TX) coils 500 with rungs on each of the two poles.

Figure 5:
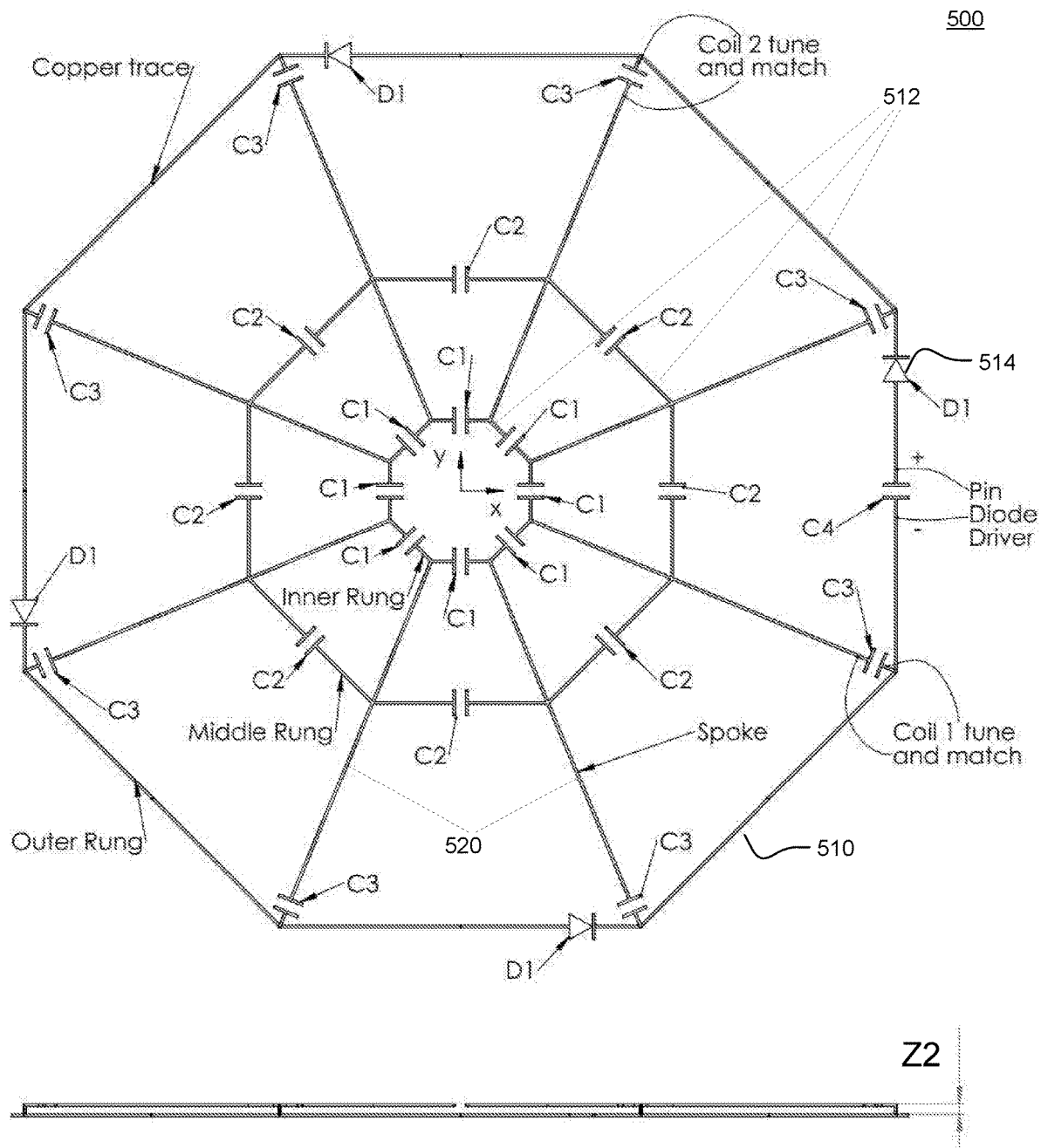
FIG. 5 shows a planar power transmit coil, according to an example embodiment.

Device 400 employs a planar power transmit (TX) coil 500, an embodiment of which is shown in FIG. 5. Device 400 comprises a planar transmit coil 500 that uses primarily circularly symmetric rung circles 510 made of multiple individual rungs or segments 512 with tailored impedances and locations to control current flow and to provide a desired RF field spatial distribution and performance characteristics. The coil is made up of largely radial spokes 520 and the largely circularly symmetric rungs 512 that connect the spokes. Spokes 520 and rungs 512 are made of a radio frequency (RF) electrical conductor material. In particular embodiments, the spokes and rungs are made from copper conductor containing electrical components. As shown in FIG. 5, in an embodiment coil 500 has 8 outer rungs 512a connecting 8 spokes 520. There are also 8 middle rungs 512b connecting the same spokes, and 8 inner rungs 512c connecting to the same spokes 520. In another implementation, 510 may be a more elliptical or other shapes. This could give an ellipsoidal or non-spherical RF excitation volume (not shown in the figures). In another implementation, the spokes did not have to be co-linear connections between the rung (not shown in the figures). In another implementation, the rung elements or segments 512 may be curved or other shaped per design choices.

The outer rungs 512a function as a current return. When an MRI transmit coil is active (ie, transmitting power), the receive coil has to be off-resonance, in order to prevent the transmit field from being affected by an RF field of the receiver coil caused by RF coupling. The prevention of coupling from the transmit coil to the receive coil caused by the transmitted power of the transmit coil is usually achieved using a detuning circuit. The outer rungs 512a contains pin diodes 514 that are used to enable or disable the TX coil 500. Capacitor C4 is a direct current (DC) blocking capacitor to allow the pin diode driver to have a circuit to drive the pin diodes with DC current. When the TX coil is enabled to be active, the pin diodes are forward biased; and when the TX coil is disabled, the pin diodes are reversed biased. In another implementation, the decoupling can be done at each Capacitors C3 location by placing an inductor in series with a pin diode, each in parallel with the capacitors C3 (not shown in the figures). This is another standard RF coil decoupling arrangement for MRI. When the pin diodes are forward biased, the capacitor C3 are in parallel with the inductor and create a resonant pair at the transmit frequency, causing those sections at the C3 locations to have a high impedance, effectively preventing any current from flowing and decoupling the coil. When the pin diodes are reversed biased, only C3 is active in the coil, and the coil functions as a resonant structure for transmitting or receiving. Capacitors C1, C2, C3, and C4 could be implemented with a single capacitor per location, or multiple capacitors in series or in parallel per location, or spread over multiple locations.

The coil can be thought of as a low pass birdcage coil. Capacitors C3 are the main tuning capacitors of the coil and are adjusted to tune the coil to the Larmor frequency of hydrogen protons, $\gamma$, in the main magnetic field $B_0$. This coil has multiple resonances, and the first resonance above DC is the one that provides the correct field distribution for the coil. This resonance results in currents in the C3 capacitors that vary as $\cos(\theta+\gamma t+k)$, where $\theta$ is the physical angle from the x axis in the x-y plane (the x-y plane is shown in FIG. 5), t is time, and k is an arbitrary constant. In another implementation, the coil can be configured as a high pass birdcage coil (not shown in the figures). In this case, the C3 capacitors would be removed from the spoke position and instead placed in each of the outer rungs. The low pass and high pass capacitor arrangements are commonly used in birdcage coils for MRI.

The capacitors C2 on the middle rungs and C1 on the inner rungs control the split of distribution of current in the middle and inner rungs. Both of these capacitors are selected so that they do not introduce secondary resonances at the Larmor frequency.

The coil has two quadrature feed points, called coil 1 tune and match and coil 2 tune and match in FIG. 5. Electrically these two feed points need to be orthogonal to each other. To function as a quadrature coil, these two feed points need to be separated by 90° in the x-y plane.

While particular embodiments circuit configuration and operational parameters have been discussed, it should be understood that this disclosure encompasses any suitable configuration and variations. The rungs location and currents may be adjusted to deliver optimized performance. For example, the rungs may be optimized in the radial location and in the Z direction to improve performance. In one implementation, the transmit coil shown in FIG. 5 has 8 segments on outer rung, 8 segments on middle rung, 8 segments on inner rung, and 8 spokes. In general, the number of segments of the rungs and the number of spokes can be varied for optimal results to suit particular applications. In particular embodiments, the outer rungs 512a may have a pin diode decoupling circuit. While three sets of rungs are discussed, one at the periphery of the coil for the current return and two in the center, the number of rungs may be adjusted. The two rungs in the center of the coil may have different capacitor values on each rung to adjust the current flow in that rung.

Coil 500 may be fed at multiple locations on the coil, primarily on the outer rung at two locations 90° from each other with two quadrature feeds with a 90° phase difference. Several nλ/2, where n is an integer, cables may be used at identical locations on the periphery of the opposite coil on the opposite pole to force the opposite coil to be exactly 180° out of phase. In particular embodiments, the decoupling circuitry could use resonant circuits around some of the capacitors that are controlled by pin diodes. This would be more appropriate for a TX coil that is also used as a transmit and receive coil, known as a T/R coil. The location of the outer rung may be offset onto a parallel plane further from the imaging field-of-view to lessen specific absorption rate (SAR). A bore shield may be used between the TX coil and a gradient coil to prevent the gradient coil from loading the TX coil.

The following paragraphs contain a technical description of the electrical characteristics of MRI device 400 and planar TX coil 500. MRI 400 uses a main magnet with two poles, as shown in FIG. 4. The main magnet drives a magnetic field into the imaging region of the magnet. That field should be uniform and is of a strength $B_0$.

During imaging, gradients vary the $B_0$ magnetic field linearly in the X, Y, and Z directions. The gradient coils pulse, and any local metallic conductors need to be designed to eliminate eddy currents. The gradients are used to determine where the signal is spatially located and ultimately their function encodes the signal so images can be made from the acquired NMR signal.

The TX coil produce a $B_1$ RF field at the Larmor frequency of hydrogen protons, γ, in the main magnetic field $B_0$. The result of this $B_1$ RF field is that hydrogen protons tip and then resonate back to equilibrium in seconds or fractions of a second depending on the material being imaged. The resonance produces a nuclear magnetic resonance (NMR) signal that is received by another RF coil, an RX coil (not illustrated). Normally the desired tip, α, of the hydrogen protons is something between 0° to 180°. A measure of the desired performance of a TX coil, is the $T_{180}$, the time that it takes to produce a 180° tip of the hydrogen protons, or sometimes called π time. If you apply an RF pulse, $B_{effective}$, for time T, $\alpha=\gamma\ B_{effective}T$. $B_{effective}$ will be explained as follows.

Only the component of the Tx $B_1$ field that is perpendicular to $B_0$ is useful. Referring to FIG. 4, $B_0$ is in the Z direction, so $B_1$ can be in either the X, or Y direction or both the X and Y directions. When $B_1$ is only in one direction, it is typically generated from a linear coil that produces an oscillating field at the Larmor frequency in only one direction at a point. When $B_1$ is in two directions, it is typically generated by a quadrature coil.

A quadrature coil can be thought up as two orthogonal linear coils driven 90° out of phase. The actual quadrature coil may physically have two orthogonal linear coils, or may be a single coil with two orthogonal modes. Either way, this creates a B1 field that rotates in the X-Y plane. This can be conceptually thought of as a uniform vector that rotates in the X-Y plane in the FOV. Such rotating fields are called circularly polarized fields. This rotating field can be thought of rotating clockwise (CW) or counterclockwise (CWW) about the Z axis. In the example shown in FIG. 4, only the CWW rotation will tip the hydrogen protons. The CW rotation effectively does nothing, and this is explained by the physics of NMR. This has consequences for the design of quadrature TX coils.

For a quadrature TX coil, there are two voltage feeds to the coil, $V^{Q1}$ and $V^{Q2}$, that are 90° out of phase and generally the same amplitude. These are mathematically $V^{Q1}=Vo*\cos(\gamma t)$ and $V^{Q2}=Vo*\sin(\gamma t)$, where γ is the Larmor frequency. These voltage feeds create separate fields from each feed. Note that the vector direction of these fields in the x, y, and z directions, and the spatial distribution of those fields will be determined by the currents created by the voltages. The fields can be calculated from the currents using the Biot-Savart Law. The field components in the z direction do not produce tips and this is explained by the physics of NMR. So only the field components in the x and y directions are included. We use the notation $\overline{B_{xy}}=B_x\vec{i}+B_y\vec{j}$, $\vec{i}$ and $\vec{j}$ being unit vectors in the x and y directions. At an arbitrary point, the field can now be described as $B^{Q1}=\overline{B_{xy}^{Q1}}*\cos(\gamma t)$, and $B^{Q2}=\overline{B_{xy}^{Q2}}*\sin(\gamma t)$.

Using the Euler formula, the fields can be separated into CW and CCW rotations using $$\cos(\gamma t) = \frac{e^{\varphi\gamma t}+e^{-\varphi\gamma t}}{2} \text{ and } \sin(\gamma t) = \frac{e^{\varphi\gamma t}+e^{-\varphi\gamma t}}{2\varphi},$$

where φ is the imaginary unit. Variables x and y now represent the complex plane, $z=x+\varphi y$. The term $e^{\varphi\gamma t}$ is a unit vector rotating CCW around the origin and $e^{-\varphi\gamma t}$ is a vector rotating CW. Using these identities and gathering only the CCW component:

$$B_{effective} = \frac{\overline{B_{xy}^{Q1}}}{2}+\frac{\overline{B_{xy}^{Q2}}}{2\varphi}$$

The field components in the previous equation can be converted to the complex plane. The magnitude of $B_{effective}$ can be solved at all points. $B_{effective}$ is proportional to the tip of the hydrogen protons from the previous equation: $\alpha=\gamma\ B_{effective}T$. $B_{effective}$ can now be used in the optimization of the planar TX coil with rungs.

The main function of the TX coil is to produce uniform tips of the hydrogen proton in the imaging FOV. The uniformity of $B_{effective}$ should be better than ±3 dB. To avoid extraneous signals from outside the FOV, the coil $B_{effective}$ should drop off better than −10 dB outside the region where the gradient coil field starts to fold over. Additionally, the drop off in $B_{effective}$ helps decrease SAR heating in the patient.

Figure 6:
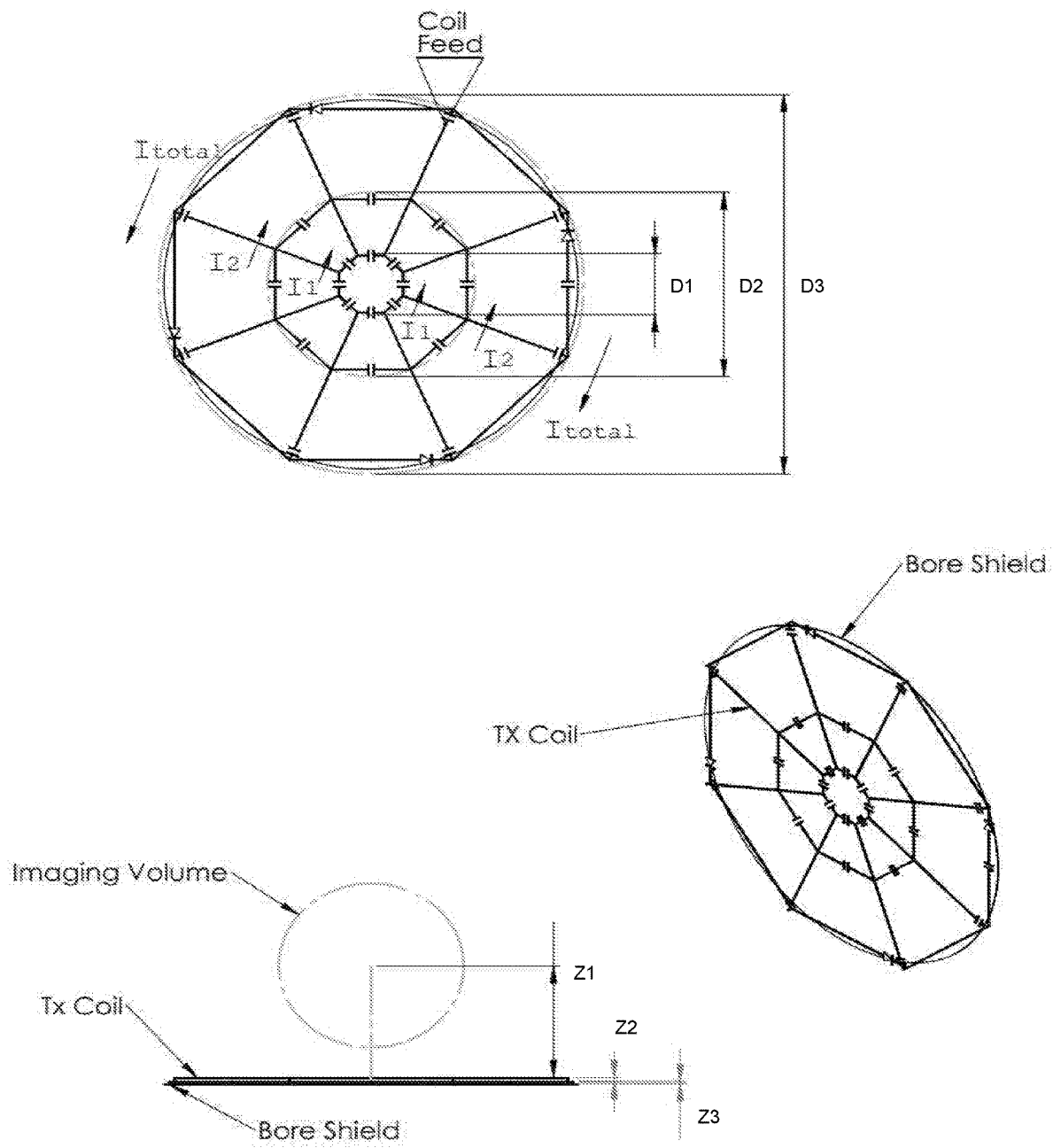
FIG. 6 shows the design variables that can be optimized for a planar power transmit coil.

FIG. 6 shows the main variables to be optimized—diameters on which the rungs are located, D1, D2, and D3, the distance the outer rungs is stepped back from the FOV, Z2, and the split of current between the middle and inner rungs, $I_2/I_1$.

After solving for these variables, capacitances C1 and C2 need to be chosen to effectively produce the desired current ratio $I_2/I_1$. This can be done experimentally or through simulation.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A magnetic resonance imaging device comprising:
    two opposing planar transmit coils facing each other, each of the two opposing planar transmit coils comprising:
        a plurality of radio frequency conducting planar rungs arranged to form concentric figures; and
        a plurality of radio frequency conducting planar spokes extending from an outermost rung of the plurality of radio frequency conducting planar rungs and connecting to each of the concentric figures; and
    a plurality of tuning capacitors for tuning each of the two opposing planar transmit coils to a resonant frequency of the magnetic resonance imaging device.

2. The magnetic resonance imaging device of claim 1, wherein each of the two opposing planar transmit coils further comprises:
    a plurality of current splitting capacitors, wherein each of the plurality of current-splitting capacitors are positioned across one of the plurality of radio frequency conducting planar rungs between two of the plurality of radio frequency conducting planar spokes.

3. The magnetic resonance imaging device of claim 1, wherein each of the plurality of tuning capacitors is positioned across a spoke of the plurality of radio frequency conducting planar spokes between the outermost rung of the plurality of radio frequency conducting planar rungs and associated with an outermost figure of the concentric figures and a second outermost rung of the plurality of radio frequency conducting planar rungs and associated with a second outermost figure of the concentric figures.

4. The magnetic resonance imaging device of claim 1, the magnetic resonance imaging device further comprising:
    a pin diode in the outermost rung of the plurality of radio frequency conducting planar rungs decoupling each of the two opposing planar transmit coils.

5. The magnetic resonance imaging device of claim 1, the magnetic resonance imaging device further comprising:
    a resonant inductor in series with a pin diode in parallel with each of the plurality of tuning capacitors for decoupling each of the two opposing planar transmit coils.

6. The magnetic resonance imaging device of claim 1, wherein each of the plurality of tuning capacitors is positioned singularly between the plurality of radio frequency conducting planar spokes on the outermost rung of the plurality of radio frequency conducting planar rungs.

7. The magnetic resonance imaging device of claim 1, the magnetic resonance imaging device further comprising:
    a first power source delivering a quadrature feed; and
    a second power source delivering a quadrature feed, wherein the first power source and the second power source have a 90° phase difference.

8. The magnetic resonance imaging device of claim 7, wherein the first power source and the second power source are applied to the outermost rung of the plurality of radio frequency conducting planar rungs at locations with 90° separation on an outermost figure of the concentric figures.

9. The magnetic resonance imaging device of claim 1,
    wherein each of the two opposing planar transmit coils has three concentric rung circles,
    wherein each rung circle of the three concentric rung circles is formed of eight rungs, and
    wherein each of the two opposing planar transmit coils has eight spokes.

10. The magnetic resonance imaging device of claim 9, further comprising:
    four pin diodes, wherein one of each of the four pin diodes is positioned across every other rung of an outermost figure of the concentric figures.

11. The magnetic resonance imaging device of claim 1, wherein each of the plurality of radio frequency conducting planar rungs and the plurality of radio frequency conducting planar spokes are positioned on a single plane.

12. The magnetic resonance imaging device of claim 1,
    wherein an outermost figure of the concentric figures is positioned on a first plane,
    wherein a remainder of the concentric figures and the plurality of radio frequency conducting planar spokes are positioned on a second plane,
    wherein the first plane and the second plane are parallel to each other, and
    wherein the first plane is offset further from a center of the magnetic resonance imaging device than the second plane.

13. The magnetic resonance imaging device of claim 1, further comprising:
    a bore shield positioned parallel to a first transmit coil of the two opposing planar transmit coils; and
    a second bore shield positioned parallel to a second transmit coil of the two opposing planar transmit coils.

* * * * *